(12) United States Patent
Willard et al.

(10) Patent No.: US 8,306,603 B2
(45) Date of Patent: Nov. 6, 2012

(54) MRI INVOLVING CONTRAST AGENT WITH TIME MODULATED CONTRAST ENHANCEMENT

(75) Inventors: Nicolaas Petrus Willard, Eindhoven (NL); Rene Theodorus Wegh, Eindhoven (NL); Jeroen Alphons Pikkemaat, Eindhoven (NL); Holger Gruell, Eindhoven (NL); Tobias Schaeffter, Blackheath (GB); Rudolf Mathias Johannes Nicolaas Lamerichs, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1054 days.

(21) Appl. No.: 11/912,674

(22) PCT Filed: Apr. 25, 2006

(86) PCT No.: PCT/IB2006/051286
§ 371 (c)(1),
(2), (4) Date: Oct. 26, 2007

(87) PCT Pub. No.: WO2006/114765
PCT Pub. Date: Nov. 2, 2006

(65) Prior Publication Data
US 2008/0200799 A1    Aug. 21, 2008

(30) Foreign Application Priority Data
Apr. 26, 2005   (EP) .................................... 05103351

(51) Int. Cl.
*A61B 5/05*   (2006.01)

(52) U.S. Cl. ........................................ 600/420; 382/128
(58) Field of Classification Search .................. 600/410, 600/411, 420; 424/9.1, 9.3–9.37; 324/300
See application file for complete search history.

(56) References Cited

U.S. PATENT DOCUMENTS

| | | | |
|---|---|---|---|
| 6,198,960 | B1 | 3/2001 | Fain et al. |
| 6,746,662 | B1 | 6/2004 | Sherry |
| 6,850,793 | B1 | 2/2005 | Miyazaki et al. |
| 2002/0127182 | A1 | 9/2002 | Sherry |
| 2004/0030239 | A1 | 2/2004 | Van Zijl |
| 2004/0058951 | A1 | 3/2004 | Lanza et al. |
| 2005/0074149 | A1* | 4/2005 | Niemeyer ............. 382/128 |

FOREIGN PATENT DOCUMENTS

| | | |
|---|---|---|
| EP | 1331012 A1 | 7/2003 |
| WO | 0047111 A1 | 8/2000 |
| WO | 0065995 A1 | 11/2000 |
| WO | 0066180 A2 | 11/2000 |
| WO | 0243775 A2 | 6/2002 |
| WO | 03063912 A1 | 8/2003 |

(Continued)

OTHER PUBLICATIONS

Balaban, R. S., et al.; Magnetization Transfer Contrast in Magnetic Resonance Imaging; 1992; Magnetic Resonance Quarterly; 8(2)116-137.

(Continued)

*Primary Examiner* — Parikha Mehta

(57) ABSTRACT

The present invention provides a method MRI imaging. By applying a time modulation to the contrast enhancement of an MRI contrast agent, the method according to the invention leads to images with improved signal-to-noise ratio in the contrast-enhanced areas, strongly suppressed unwanted signal in the unenhanced areas, and reduced artefacts, such as motion artefacts.

10 Claims, 6 Drawing Sheets

FOREIGN PATENT DOCUMENTS

WO 2004065385 A1 8/2004
WO 2005034749 A1 4/2005

OTHER PUBLICATIONS

Caravan, P., et al.; Gadolinium(III) chelates as MRI contrast agents: Structure, dynamics, and applications; 1999; Chem. Rev.; 99:2293-2352.

Gillies, R. J., et al.; pH Imaging; A review of pH measurement methods and applications in cancers; 2004; IEEE Engineering in Medicine and Biology; pp. 57-64.

Heppeler, A., et al.; Radiometal-Labelled Macrocyclic Chelator-Derivatised Somatostatin Analogue with Superb Tumour-Targeting Properties and Potential for Receptor-Mediated Internal Radiotherapy; 1999; Chem. Eur. J.; 7(5) 1974-1981.

Kimura, E.; A Tris(Znill-1,4,7,10-tetraazacyclododecane) Complex as a New Receptor for Phosphate Dianions in Aqueous Solution; 1997; J. Am. Chem. Soc.; vol. 199; pp. 3068-3076.

Meade, T. J., et al.; New magnetic resonance contrast agents as biochemical reporters; 2003; Current Opinion in Neurobiology; 13:597-602.

Shapiro, M. G., et al.; Dynamic imaging with MRI contrast agents: quantitative considerations; 2006; Magnetic Resonance Imaging; 24:449-462.

Tanttu, J. I., et al.; Synergistic enhancement of MRI with Gd-DTPA and magnetization transfer; 1992; Journal of Computer Assisted Tomography; 16(1)19-24.

Terreno, E., et al.; Ln(III)-DOTAMGly complexes: a versatile series to assess the determinants of the efficacy of pharmagnetic chemical exchange saturation transfer agents for magnetic resonance imaging applications; 2004; Investigative Radiology; 39(4)235-243.

Ward, K. M., et al.; A new class of contrast agents for MRI based on proton chemical exchange dependent saturation transfer (CEST); 2000; J. Mag. Res.; vol. 143; pp. 79.

Zhang, S., et al.; The amide protons of an ytterbium(III) dota tetraamide complex act as efficient antennae for transfer of magnetization to bulk water; 2002; Angew. Chem. Int. Ed.; 41(11)1919-1921.

Zhou, J., et al.; Chemical exchange saturation transfer imaging and spectroscopy; 2006; Progress in Nuclear Magnetic Resonance Spectroscopy; 48:109-136.

Ward, K.M. et al "Determination of pH Using Water Proton Chemical Exchange: Potential pH Sensitive MRI Contrast Agents" Mag. Res. Med, vol. 44, p. 799, 2000.

Friston, K.J. et al "Analysis of Functional MRI Time-Series" Human Brain Mapping, vol. 1, pp. 153-171, 1994.

Bandettini, Peter A. et al "Processing Strategies for Time-Course Data Sets in Functional MRI of the Human Brian" MRM, vol. 30, pp. 161-173, 1993.

Aime, Silvio et al "Novel pH-Reporter MRI Contrast Agents", Angew. Chem. Int. Ed. 2002, vol. 41, No. 22, pp. 4334-4336.

Aime, Silvio et al "Paramagnetic Lanthanide(III) Complexes as pH-Sensitive Chemical Exchange Saturation Transfer (Cest) Contrast Agents for MRI Applications", Magnetic Resonance in Medicine, vol. 47, pp. 639-648, 2002.

Zhang, Shanrong et al "Paracest Agents: Modulating MRI Contrast via Water Proton Exchange", Accounts of Chemical Research, American Chemical Society, vol. 36, No. 10, pp. 783-790, Feb. 2003.

\* cited by examiner

MRI INVOLVING CONTRAST AGENT WITH TIME MODULATED CONTRAST ENHANCEMENT

The present invention relates to magnetic resonance imaging (MRI). More particularly, the invention relates to MRI leading to images with improved signal-to-noise ratio in the contrast-enhanced areas, strongly suppressed unwanted signal in the unenhanced areas, and reduced artefacts, such as motion artefacts.

Magnetic Resonance Imaging (MRI) is one of the major imaging techniques in medicine and is one of the main carriers for molecular imaging. Images are obtained by applying a strong magnetic field, a magnetic-field gradient, and a correlated RF irradiation to a patient. During the imaging process, atomic nuclei with an intrinsic magnetic moment, in the human body mostly hydrogen atoms (protons) of water and fat molecules, which act like magnetic dipoles, become excited by the RF radiation. When the RF irradiation is stopped, relaxation of the excited nuclei causes spontaneous emission of an RF signal. As a result of applied magnetic-field gradients, the frequencies in this emitted RF signal contain spatial information and can be used to construct an image.

Sometimes the difference in MRI contrast between different tissues is not sufficient to obtain satisfactory clinical information and MRI contrast agents are then used. Nowadays, the use of contrast agents (CA) in MRI is growing. Current contrast agents comprise (super)paramagnetic materials, which influence the relaxation process of the nearby water $^1$H nuclei and so lead to a local change of the image contrast. However, after administration of the contrast agent, the change in contrast is not controlled. It depends mostly on the concentration of the contrast agents, which, in turn depends on its biodistribution. Thus, contrast improvement by current MRI contrast agents is different for every patient and can lead to images with too low or too high contrast, longer measuring times, unnecessary high doses of contrast agents and possibly negative health effects.

In most cases, areas of contrast enhancement are located within or near areas with significant MRI contrast existing already without using contrast agents. To accurately localize areas with contrast-agents uptake or to quantify the amount of contrast-agent uptake in a certain area, it is therefore necessary to take, apart from the contrast-enhanced image, a reference image as well. This reference image can be used to subtract the pre-existing contrast from the contrast-enhanced image. With the currently used contrast agents, contrast enhancement cannot be switched off after administration. Thus, reference images have to be acquired prior to administration of the contrast agent, or after clearance from the tissue, which usually takes hours to days.

The contrast-enhanced image necessarily lags the reference image by several minutes (normal clinical practice) or even many hours or days, for example to allow for macrophage-mediated contrast uptake in lymph-nodes, depending on the rate of contrast-agent uptake. In the case of molecular imaging, for example, this lag time is expected to be hours or days. Patient displacement during these lag times are considerable and subtraction of the mismatched reference image causes large errors in the quantification. Especially in cases of little contrast-agent uptake, such as targeted molecular imaging, these errors can easily exceed the actual contrast enhancement. Hence, accurate quantification is difficult or even impossible. For example, in case of targeted molecular imaging, the contrast agent comprises a targeting ligand that has to bind to target molecule receptors for the disease of interest and subsequently the unbound contrast agent has to be cleared from the rest of the body. This whole process takes hours to even days and acquiring a reference image prior to administration is now essential since the image after binding of the CA does not comprise any morphological information.

A problem that thus may arise during MRI imaging is that of motion the patient, and thus of the body, causing motion artefacts. These motion artefacts can be caused by motion of the complete body, or by motion of a part of the body, e.g. an arm or leg of the patient, during the imaging sequence. The motion of the entire body during the imaging sequence generally results in a blurring of the entire image with ghost images in the phase encoding direction. Movement of a small portion of the imaged object results in a blurring of that small portion of the object across the image.

It is an object of the present invention to provide a device and a method for performing magnetic resonance imaging (MRI) which leads to images with improved detectability of contrast enhancement.

The above objective is accomplished by a method and device according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

In a first aspect, the present invention provides a method for MRI imaging, the method comprising:
  after administration of a contrast agent by a patient,
  acquiring at least a part of a reference MRI image of at least a part of a body of the patient after applying a first external stimulus to said contrast agent,
  acquiring at least a part of a contrast enhanced MRI image of at least the part of the body of the patient after applying a second external stimulus to said contrast agent, and
  determining effect, e.g. presence, of contrast agent in the part of the body from a comparison, e.g. difference, between the contrast enhanced MRI image and the reference image.

The first and the second external stimulus preferably are different from each other. According to embodiments of the invention, the first external stimulus may comprise applying a first RF saturation pulse and the second external stimulus may comprise applying a second RF saturation pulse, the first and second RF saturation pulses differing from each other in at least one of power, offset frequency, shape, multiplicity, duration of intervals of said RF saturation pulse. For example, in one embodiment, the first external stimulus may be a stimulus with zero amplitude, i.e. in fact no stimulus at all, so as to not switch on the contrast agent. In an alternative embodiment, the first and the second external stimuli may have at least one different parameter, e.g. different frequencies.

The present invention furthermore provides a method for MRI imaging, the method comprising:
  repeatedly acquiring an image or a part of an image, hereby deliberately modulating contrast enhancement of a contrast agent in time by applying a time-varying external stimulus to said contrast agent, the time-varying external stimulus having a known time course,
  thereafter, separately constructing each image or part of the image,
  from the separately constructed images, determining an intensity time course of each image or each part of the image, and
  correlating the intensity time course with the known time course of the externally applied stimulus or using the intensity time course for extracting tissue parameters influencing the dynamic response of the contrast enhancement as a result of changes in the external stimulus.

The present invention also provides a method for MRI imaging after administration to a patient of a contrast agent of the type where at least a part of a reference MRI image of at least a part of a body of the patient is acquired and at least a part of a contrast enhanced MRI image of at least the part of the body of the patient is acquired, the method comprising:
  for the acquisition of at least the part of the reference MRI image: activating a first external stimulus for said contrast agent,
  for the acquisition of at least the part of the contrast enhanced MRI image: activating a second external stimulus for said contrast agent, and
  determining effect, e.g. presence, of contrast agent in the part of the body from a comparison, e.g. difference, between the contrast enhanced MRI image and the reference image.

The first and the second external stimulus preferably are different from each other. In one embodiment, the first external stimulus may be a stimulus with zero amplitude, i.e. in fact no stimulus at all, so as to not switch on the contrast agent. In an alternative embodiment, the first and the second external stimuli may have at least one different parameter, e.g. different frequencies.

The method of the present invention leads to MRI images with improved detectability of contrast enhancement, a high signal-to-noise ratio and with reduced motion artefacts. According to embodiments of the invention, suitable contrast agents to be used with the method of the invention may comprise at least one exchangeable entity having a nuclear spin and a nuclear spin resonance frequency. The exchangeable entity may for example be a proton, a water molecule or a phosphate group.

In embodiments of the invention, the exchangeable entity may have a first and a second exchangeable position, wherein during MRI imaging the exchangeable entity changes from the first to the second exchangeable position, hereby inducing a change in its nuclear spin resonance frequency.

In particular embodiments according to the present invention, the contrast agent may be a CEST contrast agent. For example, the contrast agent may be a Yb-DOTAM-G3 complex, which is formed of a Yb-DOTAM paramagnetic complex covalently attached to a PPI dendrimer as a carrier. An advantage of this molecule is that is comprises about 112 exchangeable protons which leads to an increase of the sensitivity of the MRI technique.

According to embodiments of the invention, the time-varying external stimulus may be performed by applying a RF saturation pulse, hereby varying at least one of power, offset frequency, shape, multiplicity, duration or intervals of said RF saturation pulse for modulating the contrast enhancement. The RF saturation pulse may comprise shaped RF pulses, composite RF pulses, RF pulse trains, continuous-wave RF irradiation or combinations thereof.

In embodiments of the invention, the contrast enhancement may be modulated by switching the contrast enhancement on and off.

In a second aspect, the present invention provides a device for performing MRI imaging. The device comprises:
  means for applying an external stimulus for modulating contrast enhancement of a contrast agent administered to a patient,
  means for acquiring at least a part of a reference MRI image of at least a part of a body of the patient after applying a first external stimulus to said contrast agent, and for acquiring at least a part of a contrast enhanced MRI image of at least the part of the body o the patient after applying a second external stimulus to said contrast agent, and
  calculating means for determining effect, e.g. presence, of contrast agent in the part of the body from a comparison, e.g. difference, between the contrast enhanced MRI image and the reference image.

The present invention furthermore provides a device for performing MRI imaging, the device comprising:
  input means for inputting parameter data, e.g. an intensity course, for the formation of a time-varying external stimulus,
  means for applying a time-varying external stimulus for modulating contrast enhancement of a contrast agent, being such that the time-varying external stimulus is based on the parameter data, e.g. intensity course, as input,
  image generating means for separately constructing each image or part of the image,
  first calculating means for determining an intensity time course of each constructed image or part of the image, and
  second calculating means for correlating said determined intensity time course with the known parameter data, e.g. intensity course, of the externally applied time-varying stimulus or for using the determined intensity time course for extracting tissue parameters influencing the dynamic response of the contrast enhancement as a result of changes in the external stimulus.

According to embodiments of the invention, the means for applying a time-varying external stimulus may be a RF pulse generating means for applying a time-varying RF saturation pulse. The RF saturation pulse may comprise shaped RF pulses, composite RF pulses, RF pulse trains, continuous-wave RF irradiation or combinations thereof.

In embodiments of the invention, the first calculation means and the second calculation means may be part of a computer.

The present invention furthermore provides a computer program product which, when executed on a processing device, performs any of the methods of the present invention.

The present invention furthermore discloses a machine readable data storage device storing the computer program of the present invention and a controller for an MRI imaging device, the controller comprising means for obtaining data relating to formation of a time-varying external stimulus and control means for controlling a means for applying a time-varying external stimulus to a contrast agent in accordance with the data obtained.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
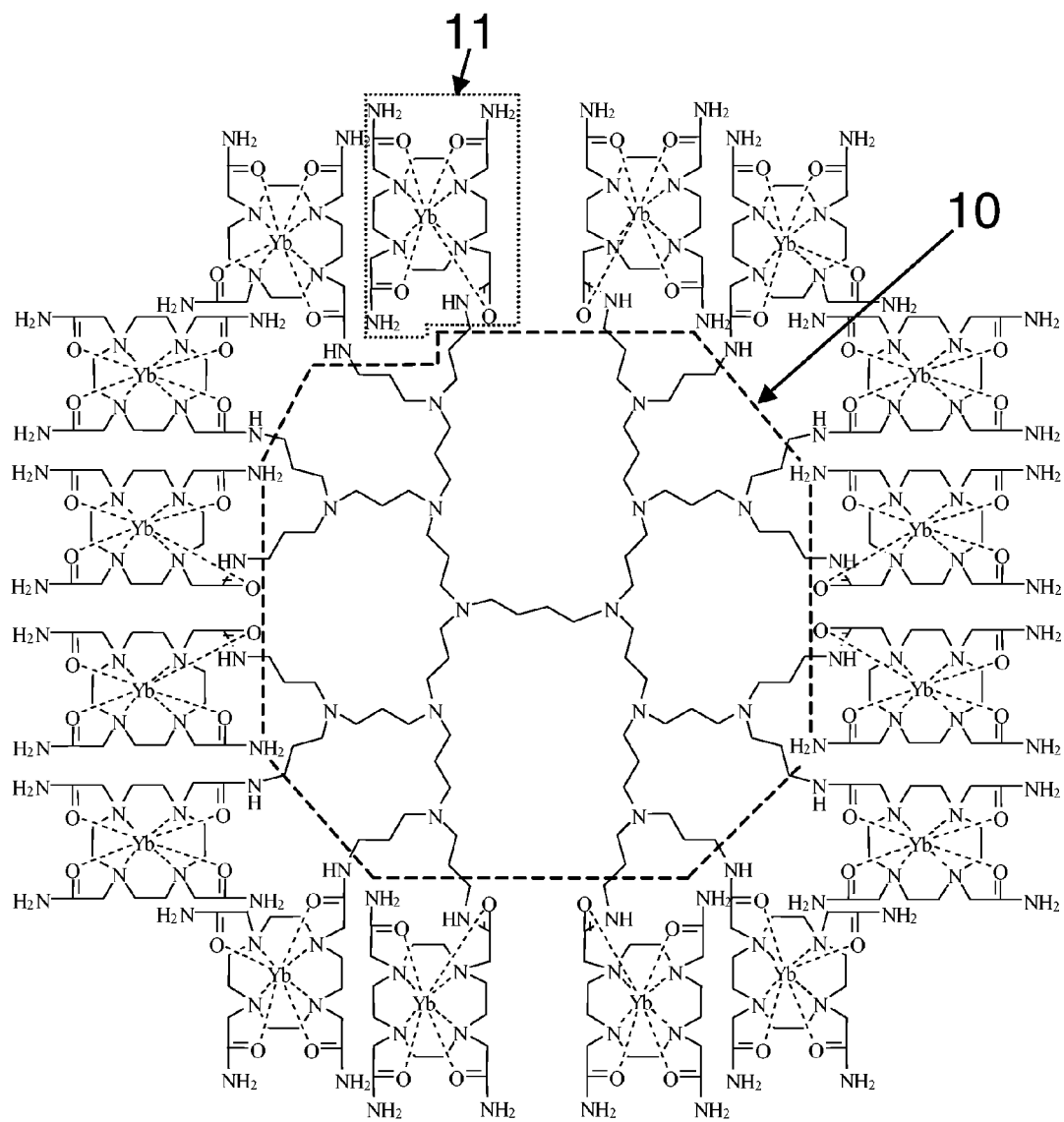
FIG. 1 shows the structure of Yb-DOTAM-G3.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The present invention provides a method and device for performing magnetic resonance imaging (MRI) leading to images with high signal-to-noise ratio (SNR) in the contrast-enhanced areas, strongly suppressed unwanted signal in the unenhanced areas, and reduced artefacts such as e.g. motion artefacts. According to the invention, this is achieved by using time-modulated contrast enhancement. In a first aspect of the invention, a method is provided for performing MRI. Instead of two images, i.e. one contrast-enhanced image taken after contrast agent uptake and one reference image taken before contrast agent uptake, as is the case in the known prior art MRI methods, the present invention acquires at least two images, for example a time series of images or parts of images, after contrast agent uptake only, in which the contrast enhancement is deliberately varied or modulated in time according to a predetermined protocol and as a result of a time-varying external stimulus, such as e.g. a time-varying RF (radio frequency) saturation pulse (see further). With "a part of an image" may be meant, for example, one or more slices, a part of a multi-slice acquisition, or one or more lines in k-space. The at least two images may comprise a reference MRI image and a contrast enhanced MRI image of a part of a body, a series of part of a reference MRI image and a part of a contrast enhanced image of a part of a body until reference images and contrast enhanced images for all parts of the image to be obtained are acquired; or a time series of images or parts of images.

Herefore, the method according to the present invention makes use of contrast agents of which the contrast can be modulated in time. An example of such contrast agents are agents of which the contrast enhancement may be modulated in time by applying, e.g. an RF-pulse protocol. Suitable contrast agents which may be applied with the method of the present invention should therefore comprise at least one exchangeable entity, such as e.g. a proton, a phosphate group, a water molecule, having a nuclear spin and a nuclear spin resonance frequency, which may be temporarily saturated with e.g. a suitable RF-pulse protocol. With an exchangeable entity is meant an entity having a first exchangeable position and a second exchangeable position, wherein during the MRI experiment, the exchangeable entity changes from the first to the second position, hereby inducing a change in its nuclear spin resonance frequency. By changing from the first to the second exchangeable position, the exchangeable entity should thus generate different signals, i.e. different nuclear spin resonance frequencies, depending on where they are, i.e. at the first exchangeable position or at the second exchangeable position. Preferably, the contrast agent may comprise an as high as possible number of exchangeable entities, i.e. up to $10^6$, for example 112, because the more exchangeable entities the contrast agent comprises, the better the image intensity change, e.g. the contrast, and the sensitivity of the MRI method according to the first aspect of the invention will be, as the image intensity change and the sensitivity of the MRI method depends on the extent of magnetic saturation of the exchangeable entities and of the chemical exchange rate. Furthermore, the exchangeable entities should have a nuclear spin resonance frequency well away from the spin resonance frequency used to generate the image, e.g. the water peak in the case of proton imaging.

The method according to an embodiment of the first aspect of the present invention will be discussed in detail hereinafter. In a first step, an image or part of an image is acquired repeatedly, i.e. more than twice, while the contrast enhancement is deliberately modulated in time as a result of a time-varying external stimulus, which may, for example, be a time-varying RF saturation pulse for saturating the exchangeable entity of a suitable contrast agent. Part of an image may be one or more slices, a part of a multi-slice acquisition, one or more lines in k-space, . . . . The above first step of the method may then be repeated until all parts of the image have been repeatedly acquired. The exchangeable entity may, for example, be a hydrogen atom or proton, a phosphate group, a water molecule, or any other suitable exchangeable entity.

In a next step, every image or every part of an image is separately reconstructed. This may be done by applying Fourier transformations in the spatial directions. In the case of non-Cartesian sampling, e.g. radial, the data are first placed onto a Cartesian grid before applying Fourier transformations. Also other means of reconstruction can be used, such as projection reconstruction, or combinations of different methods. Then, the intensity time course, i.e. the variation of the intensity of the images as a function of time, is correlated with the known time course of the externally applied modulation, pixel by pixel or voxel by voxel, for the sequence of images or parts of images. This correlation may be performed by means of statistical analysis, for example by using a student t-test, cross correlation, or temporal statistics. If this is done for all pixels or for all voxels in an image, a so-called probability map is obtained. A high value of a pixel or voxel in this probability map means a high probability for the presence of contrast agent in this pixel or voxel, a low value means a low probability. Alternatively to a correlation analysis, a Fourier-transform along the time-domain may be applied to extract the modulation frequencies.

In the above-described way, as compared to normal time averaging, detection of contrast agent is improved since spurious time-variations are significantly suppressed.

In a preferred embodiment of the first aspect of the present invention, the time-modulated contrast enhancement method is applied by using chemical exchange saturation transfer (or CEST) contrast agents. In case of CEST contrast agents, the at least one exchangeable entity may be a proton. CEST agents are known for several years and first proposed as MRI contrast agents by K. M. Ward, A. H. Aletras and R. S. Balaban, in J. Mag. Res. 143, 79 (2000). CEST is based on a RF signal which is used to selectively saturate the magnetization of a specific hydrogen nucleus in the molecules of the contrast agent. As already discussed, the CEST agent may, according to the present invention, comprise a plurality of exchangeable protons, preferably as many as possible, up to $10^2$, preferably up to $10^4$, still more preferred up to of $10^6$, in order to obtain an increased intensity of the resulting image. Furthermore, the exchangeable protons of the CEST contrast agent should have a resonance frequency well away from the spin resonance frequency used to generate the image, e.g. the water peak in the case of proton imaging.

An advantage of a CEST agent is that image contrast can be switched on and off at will. Furthermore, CEST agents are known to only give the contrast enhancement by pre-saturation with an appropriate RF signal. This means that the reference images and the contrast-enhanced image can be acquired with minimal time lag by using no or off-resonance pre-saturation and on-resonance pre-saturation respectively.

The on/off function in combination with the method according to the present invention, i.e. with time-modulation of the contrast enhancement, is used to improve sensitivity, to reduce movement artefacts and to measure kinetic processes in the body. Another option is to adjust the pre-saturation pulse to obtain optimized contrast. This can be done since the induced contrast depends on the frequency of the pre-saturation RF pulse, pulse method and amplitude.

A suitable CEST contrast agent with adjustable contrast which may be used according to this embodiment and with the method of the present invention may be a molecule which comprises a carrier with at least one (super)paramagnetic particle/ion and hydrogen atoms or protons, which can undergo chemical exchange with the main water pool in the human body. Preferably, the contrast agent may comprise multiple paramagnetic ions per particle/molecule. This provides a very high number, i.e. up to $10^2$, preferably up to $10^4$, still more preferred up to $10^6$, for example 112, of exchangeable protons with a resonance frequency well away from the water peak. Preferably, lanthanide salts may be used because it is known that chemical shifts of protons that are situated close to a paramagnetic ion can be very large. Most preferred, ytterbium (Yb) salts may be used as a molecule with multiple (super)paramagnetic particles per ion and hydrogen atoms. Preferred candidates for groups with exchangeable hydrogen atoms are amides, but other groups may also be possible, for example amines, imines, urea, imides, bound water molecules, phosphates, alcohols, aldehydes, ketones, carboxylic acids, phenols and thiols. The range of proton exchangeable groups may be very large and may, for example, furthermore comprise boron, carbon, nitrogen, oxygen, silicon, phosphor, sulphur atoms.

An example of a suitable contrast agent which has all the above described properties may comprise a poly(propylene imine) or PPI dendrimer 10 functioning as carrier, with Yb-DOTAM complexes 11 as a contrast agent covalently attached to it. In this example, the number of exchangeable protons is 112. One of the molecules that has been studied in more detail is Yb-DOTAM-G3, see FIG. 1. This molecule may be used in the same concentration range as known contrast agents, which is in the range of 1 to 10 μmolar.

Figure 2:
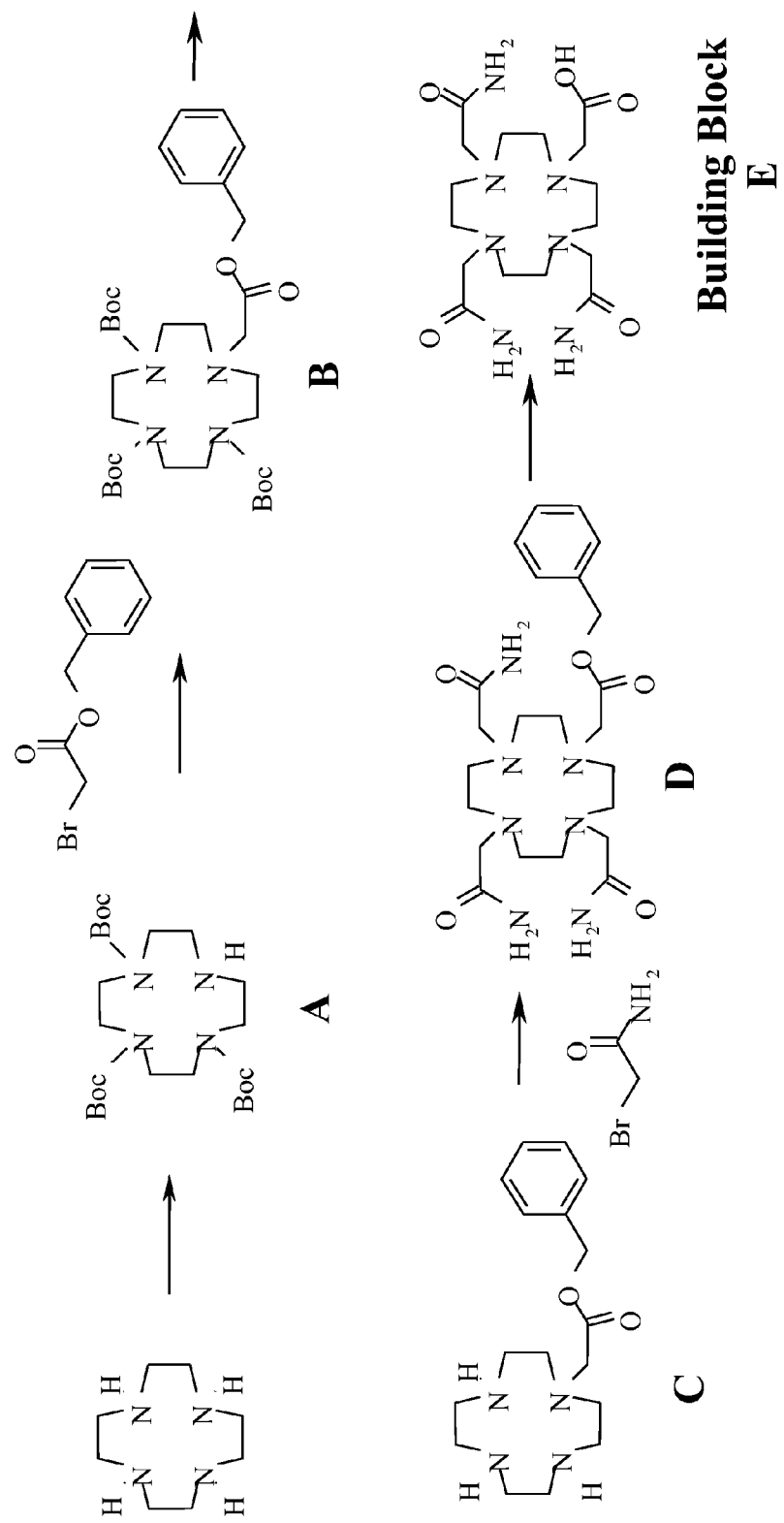
FIG. 2 and FIG. 3 illustrate the synthesis of Yb-DOTAM-G3.

A synthesis method of Yb-DOTAM-G3 will be described hereinafter. The synthesis of the 'building block' or paramagnetic complex is illustrated in FIG. 2. The synthesis is started from cyclen, which is a commercially available compound e.g. from Aldrich or Macrocyclics. The molecules A, B and C in FIG. 2 are known from literature. Molecule A and its synthesis has been reported in a.o. "E. Kimura, J. Am. Chem. Soc., 1997, 199, 3068-3076". Molecule B has been reported in WO 2004065385, Molecule C has been reported in "A. Heppeler et al., Chem. Eur. J. 1999, 5, 7, 1974-1981".

Molecule A can be prepared by slowly, i.e. within 3 hours, adding a solution of di-tert-butyl dicarbonate (7.9 g, 36 mmol) in $CHCl_3$ (100 mL, passed through $Al_2O_3$) to a solution of cyclen (2.2 g, 13 mmol) and triethylamine (5.5 mL, 39 mmol) in $CHCl_3$ (120 mL) at room temperature. The reaction mixture is stirred for 24 hours at room temperature, and the organic solvent is removed under reduced pressure. The remaining residue is purified by silica gel column chromatography (hexanes/AcOEt) to provide molecule A as a colorless, amorphous solid (4.4 g, 72%) [E. Kimura, J. Am. Chem. Soc., 1997, 199, 3068-3076].

The tri-BOC protected molecule A (15.2 g) is then dissolved in 20 mL of acetonitrile, after which 19 mL of diisopropylethylamine and 7.9 g of benzylbromoacetate in 10 mL acetonitrile are added. The solution is heated up to 60-65° C. and stirred overnight under an argon atmosphere. The mixture is then concentrated by evaporation of the solvent and dissolved in dichloromethane. The solution is washed with 1 M NaOH. The organic layer is dried with $Na_2SO_4$ and thereafter reduced by evaporation and co-evaporation with toluene. The pure product, molecule B, is isolated by silica column chromatography using hexane/ethyl acetate(1/1) as eluent. The yield is about 90%.

Molecule B (6.22 g) is dissolved in 60 mL dichloromethane and 60 mL trifluoroacetic acid (TFA). The solution is stirred under a nitrogen atmosphere. After 3 hours the solvents are evaporated and another portion of TFA (40 mL) is added. After 2 hours of further stirring the TFA is evaporated and the remaining mixture is co-evaporated twice with toluene, leaving the crude TFA-salt of molecule C as an oil, of which then 10 g is used in a following step without further purification. The oil is dissolved and stirred in 45 mL DMF and 31 mL diisopropylethylamine. Then, 4.7 g bromo acetamide is added and the mixture is stirred for two days at 50° C., during which time a precipitate is developed. The mixture is brought in 600 mL ether, is stirred and the brown precipitate is isolated by filtration and washing with ether. The solid is then washed four times with portions of 25 mL of 25% $NH_3$ solutions in water and finally with 30 mL of water. Drying under vacuum at 40° C. results in a white solid product of molecule D (yield=85%).

Molecule D (1.7 g) is then hydrogenated at 70 psi overpressure in 100 mL water using Pd/C (10%) as catalyst. The mixture is filtered over celite, the celite is washed with some water and the filtrate is freeze dried and then dried over $P_2O_5$ in vacuum to afford 1.1 gram of a fine white hygroscopic powder of molecule E.

Figure 3:
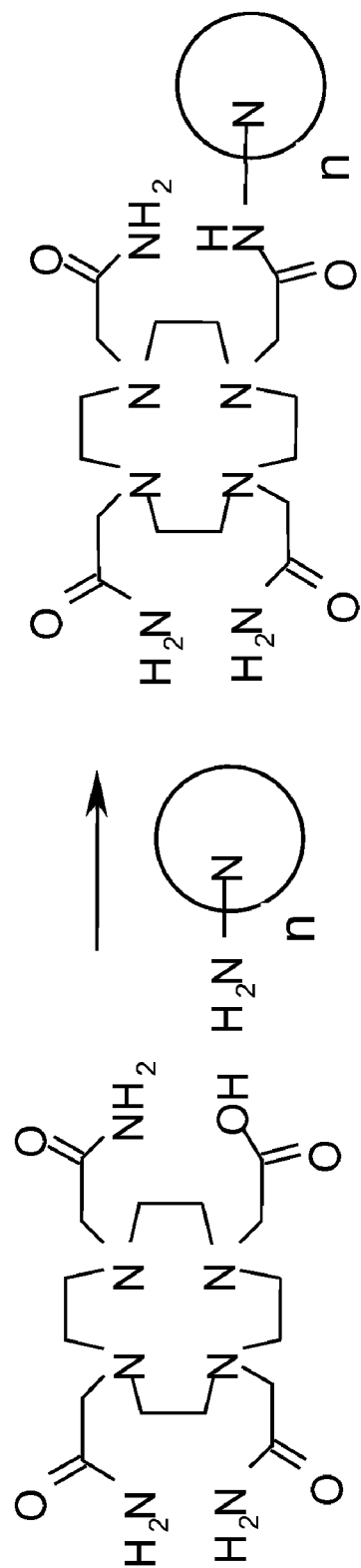

For the coupling of molecule E to the carrier, in the example given to a PPI dendrimer, the amide coupling agent HBTU (O-(benzotriazol-1-yl)-N,N,N',N'-tetramethyluronium hexafluorophosphate) is used. The coupling of the paramagnetic complex to the dendrimer is illustrated in FIG. 3. For convenience, the dendrimers are denoted as circles. The dendrimers used are commercially available poly(propylene imine) (PPI) dendrimers (from Aldrich under the name DAB-Am-X or from SyMO-Chem) with a diaminobutane (DAB) derived core. The most used name for those dendrimers is DAB-Am-X, wherein X refers to the number of surface amino groups. In this synthesis, DAB-Am-16 has been used in order to obtain a DOTAM-G3 complex.

For the coupling of molecule E to the G3 PPI dendrimer, 0.25 mL diisopropylethylamine is added to a mixture of 164 mg HBTU in 1 mL dry DMF. Molecule E (172 mg) is added and the mixture is stirred until a clear solution is acquired. This may take about 5 to 10 minutes. The third generation PPI-dendrimer DAB-Am-16 (41 mg) in 1 mL dry DMF is then added and the solution is stirred overnight under an inert atmosphere of nitrogen. The mixture is poured into 40 mL of stirred ether giving a precipitate; the ether is replaced by another portion of ether (washing step), and the precipitate is dried. Finally, the precipitate is dissolved in water and triethylamine and this solution is dialyzed using a membrane with a molecular weight cut-off of 1000 and using 1.2 L of water and 20 mL of triethyl amine as washing solvent. After overnight dialysis, the washing solution is replaced by 1.2 L of water and dialysis is continued for another 24 hours. Freeze drying of the solution in the dialysis tube gave ca. 200 mg of a fluffy white product, which in the further synthesis will be called molecule II.

A last step in the synthesis is the complexation with $Yb^{3+}$ ions. For the formation of the Yb-DOTAM-G3 complex a solution of 0.1 µmol $YbCl_3$ in 5 mL water is added dropwise to a stirring solution of 49 mg (0.1 mmol) of molecule II in 8 mL water. Subsequently, the solution is heated up to 60° C. for 2 hours while stirring, meanwhile maintaining a pH of 7 to 8 by adding small drops of $NH_4OH$. The solution is dialyzed for 24 hours using a membrane with a molecular weight cut-off of 500 and running water as washing solvent. Freeze drying of the solution yields a white powder in a yield of ~80%.

As an alternative to lanthanide ions, all other paramagnetic ions, such as e.g. transition metal ions, may also be used.

According to this preferred embodiment of the first aspect of the invention, the modulation of the contrast enhancement may be accomplished by varying the RF power or the offset frequency of the saturation pulse for saturating the plurality of exchangeable entities, in the example given the plurality of protons, of the CEST agent.

According to this embodiment, a modulation protocol may be to first acquire a number of images, for example 1 to 10 images and preferably 1 image, with the saturation pulse on, then a number of images, for example 1 to 10 images and preferably 1 image, with the saturation pulse off, then a number of images, for example 1 to 10 images and preferably 1 image, with the saturation pulse on again, etc. The accuracy of the method increases with every repeat. Typically, an experiment may comprise 10 repeats of on/off series. In principle, images may be acquired as long as is comfortable for the patient, which may typically be within a time period of about 10 minutes. Depending on the scan time of an individual image, the total series may comprise at least two, but up to several thousands of images. Since it is expected that build-up of contrast enhancement after switching-on the RF saturation pulse protocol takes at least about 0.1 seconds, the number of modulations may also be at least two to up to several thousands. A practical example, however, would be about 20 modulations with about 50 images per modulation which may be a total of about 1000 images.

Next, all individual images may be reconstructed using Fourier transform, with regridding in case of noncarthesian k-space trajectories, sometimes in combination with other techniques such as projection reconstruction. After reconstruction of the individual images, the final contrast-enhanced image may be reconstructed in a similar way as is commonly used in the field of functional MRI (fMRI), which is a method to map the various functional areas of the brain. In an fMRI examination, the patient has to perform a very specific task, e.g. a finger tapping task. The activity in the area of the brain involved in this task will increase, resulting in a subtle change of the contrast, which change is then detected by MRI. Also in the fMRI experiment the active periods and rest periods are interleaved. Important to note is that in fMRI, in general, no contrast agents are used.

If in the above-described embodiment with on is meant maximum or 100% enhancement and with off is meant 0% enhancement, in other embodiments according to this first aspect of the invention, the same protocol may be used but now with a lower percentage of enhancement, for example, 50% or 25% enhancement, instead of maximum or 100% enhancement. Within an experiment of, for example, 10 repeats, the percentage of enhancement may, as an additional variation, be varied in the respective on periods. The actual images will reflect the additional variation and further increase the specificity of the correlation map. A further benefit of using less than 100% enhancement is that it is reached much faster in time. In combination with time averaging or correlation analysis this may result in an improved over-all sensitivity.

As already described in the general embodiment of the invention, the intensity time course of a certain pixel of each image may, in this preferred embodiment, also be statistically correlated with the known time course of the time-modulating externally applied RF saturation pulse signal by, for example, using a student t-test, cross correlation, or temporal statistics. If this is done for all pixels in the image, a so-called probability map is obtained. A high value of a pixel in this correlation map means a high probability for the presence of contrast agent in this pixel, a low value means a low probability. As an alternative to a correlation analysis, a Fourier-Transform along the time-domain could be applied to extract the modulation frequency.

Unwanted sources of intensity variation between the on and the off images, such as movement of the patient, such as by cardiac, respiratory and other motion, are usually not correlated with the time course of the modulation protocol and will therefore be strongly suppressed in the correlation map. This is an important advantage with respect to the prior art methods.

According to a further embodiment of the first aspect of the invention, the variation of contrast enhancement in time may be combined with noncarthesian k-space trajectories and segmented acquisition methods, in order to further optimize the detection of contrast enhancement. The combination these techniques, also called radial imaging, may be advantageous to reduce motion artefacts. This embodiment will be described by means of using a CEST agent, but it has to be understood that this is not limiting to the invention and that also other contrast agents may be used.

Figure 4:
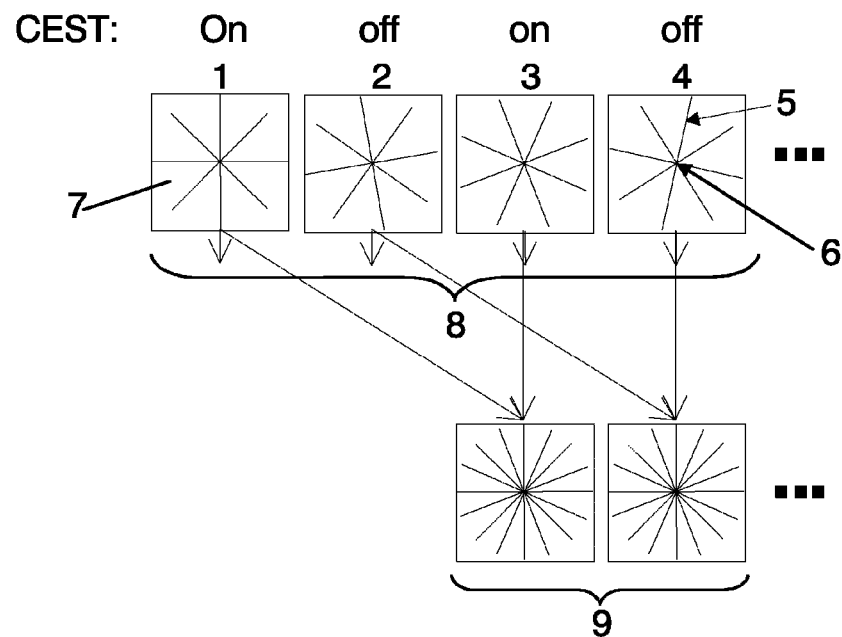
FIG. 4 illustrates a radial encoding scheme in combination with modulating the CEST effect.

FIG. 4 shows an example of a time series using a segmented acquisition of radial trajectories in k-space, acquiring segments 1 to 4, where the CEST effect is switched on/off between the segments 1 to 4. All k-space lines 5 traverse through the center 6 of the k-space 7, therefore, the image contrast is frequently updated since the radial acquisition method samples more densely the central k values (signal intensity) as compared to the high k values (resolution). As a result, undersampling with the radial readout method does not affect the images contrast but merely results in images with lower resolution. Furthermore, each segment 1 to 4 allows the reconstruction of a low-resolution image 8. As explained the undersampling in the radial method mainly affects image resolution. Herefore, again Fourier transform and regridding may be used in combination with other methods, such as e.g. projection reconstruction. Furthermore, the combination of segments 1 to 4 allows for the reconstruction of high-resolution images 9. The resolution is now better since a higher number of readouts of the high k-values is realized. In that way, the correlation analysis can be performed on different spatial and temporal resolution levels. The main advantage is an increase in image speed since from one radial acquisition it is possible to reconstruct the correlation images, albeit with low resolution, and the high resolution anatomical image.

It has to be understood that the above-described technique is a combination of two methods for data acquisition, i.e. radial k-space filling and segmented acquisition. These acquisition techniques may, in some cases, be necessary for optimal detection of the time-modulated contrast enhancement.

The method according to the first aspect of the invention leads to improved and more sensitive MRI imaging with an improved signal-to-noise ratio. It suffers less from movement artefacts and makes an improved detection of MRI labels at low concentration possible. It may be used for contrast-enhanced MRI in general, for separating contrast-agent induced signal changes from other, unwanted, signal variations. Furthermore, it may be applied for pH, temperature or other parameter mapping, such as e.g. the presence of certain metal ions, for example Ca2+ ions, or metabolites, for example glucose or lactate, to find for example small lesions, i.e. early signs of cancer, ischemia.

Figure 5:
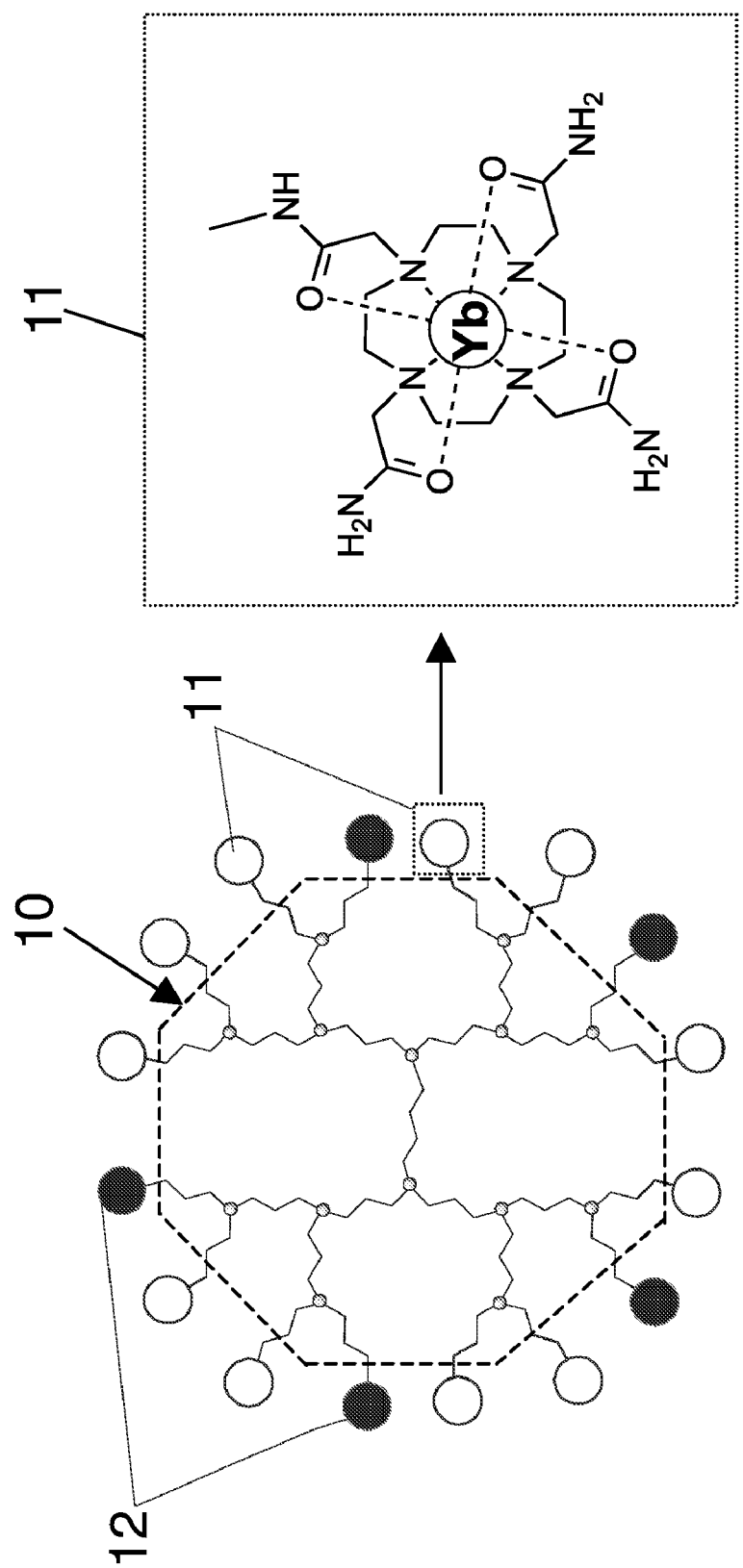
FIG. 5 illustrates a dendritic CEST contrast agent for targeted molecular imaging according to an embodiment of the invention.

The method according to this first aspect of the present invention may be used for, for example, targeted molecular imaging. For use in targeted molecular imaging, also a targeting ligand 12 may be attached to the dendrimer 10, see FIG. 5. Suitable targeting ligands 12 may be, but are not limited to, cyclic oligonucleotides corresponding to the Arg-Gly-Asp (RGD) or Asn-Gly-Arg (NGR)-containing peptide motif for angiogenesis, Annexin V for apoptosis, antifibrin or oxidized LDL (oxLDL) for arteriosclerosis. FIG. 5 schematically illustrates the same structure, i.e. Yb-DOTAM-G3, as in FIG. 1, only now a few of the CEST agent groups 11 are replaced by a targeting ligand 12.

Instead of a dendrimer as a carrier, as in the previous examples, a linear polymer, e.g. polyethylene imine, polyarginine, polyasparagine, polylysine or polyglutamine, or a liposome or a (lipid) micelle or any particle with a phospholipid or polymeric shell of core, e.g. phospholipids particles used by Wickline and Lanza in US 2004/0058951, may be used as a carrier. The latter may have the advantage that more paramagnetic ions may be incorporated in one particle, which may improve the sensitivity even more.

Instead of Yb, other (super)paramagnetic particles, such as e.g. iron oxide may be used. In other embodiments, superparamagnetic iron oxide particles coated with dextran or a polymer containing amide protons may be used. Such contrast agents may usually be taken up by macrophages and transported to e.g. the liver, which necessitates a large time lag between the contrast-enhanced and the reference image.

One of the main applications of the method according to the first aspect of the invention may be in the area of molecular imaging in which there is a large time lag and error between reference and contrast agent imaging. To obtain sufficient sensitivity, preferably CEST agents with multiple paramagnetic ions per particle/molecule may be used, because they provide a very high number of exchangeable protons with a resonance frequency well away from the water peak. The multiple paramagnetic ions can be attached covalently or non-covalently to a carrier, which can be e.g. a dendrimer, a linear polymer or a liposome, as was discussed above. In the case of targeted molecular imaging a targeting ligand that will bind to the target molecule of interest in the body is also attached to the carrier.

It has, however, to be understood that other agents than CEST agents may also be used to obtain the benefits of this invention.

Figure 6:
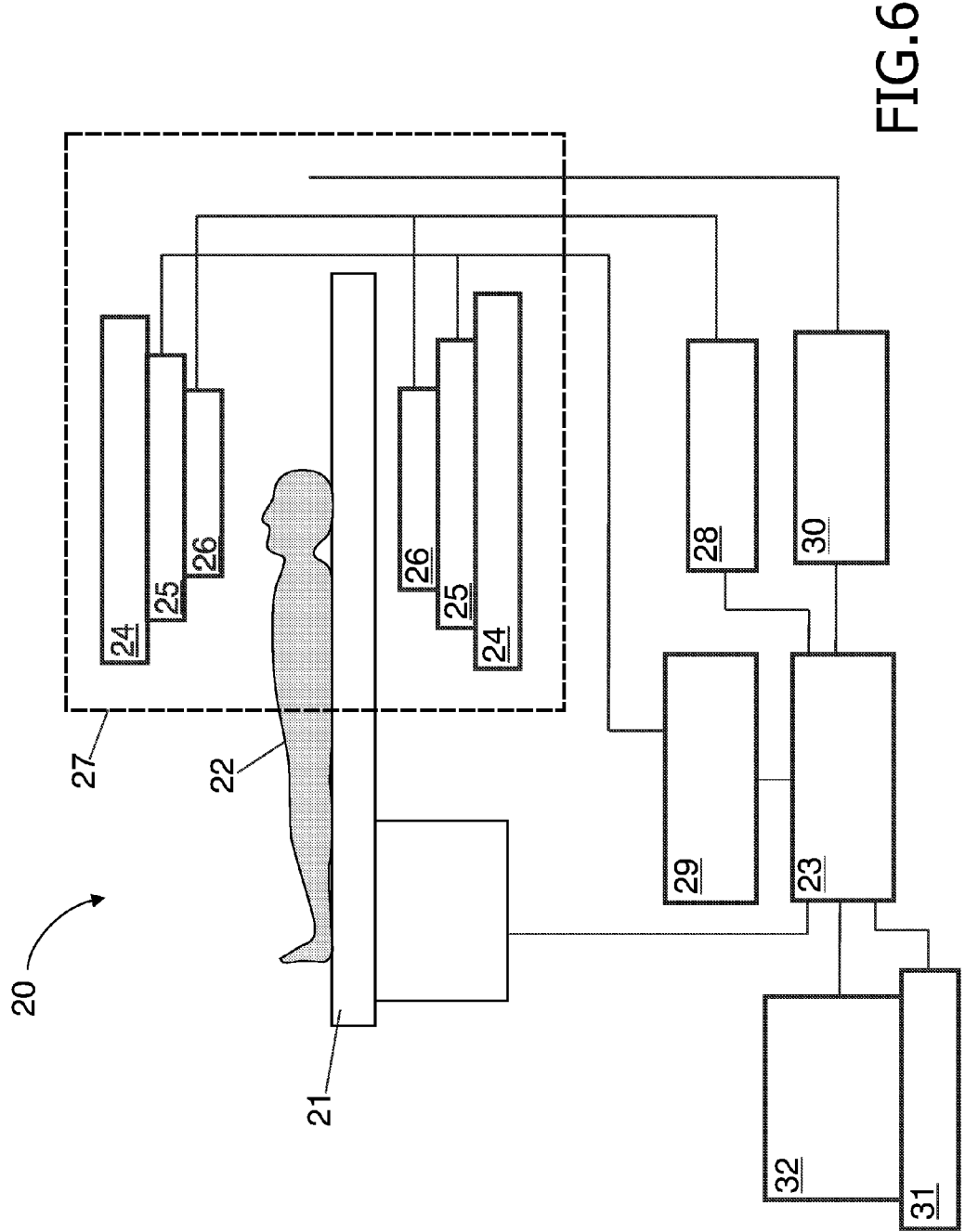
FIG. 6 illustrates a MRI scanner for performing the method according an embodiment of the invention.

In a second aspect of the invention, an MRI scanner 20 for performing the MRI method as described in the first aspect of the invention is provided. The MRI scanner 20, which is illustrated in FIG. 6, comprises a narrow table 21 on which the object to be imaged, in most cases a patient 22, is laid down. The object to be imaged may also be, for example, an animal. In that case, MRI may be applied for animal imaging e.g. for research purposes. The narrow table 21 can slide inside a tunnel-like tube within the scanner 20 and can be controlled by a controller 23 such as e.g. a computer. The positioning accuracy of the table 21 depends on the kind of table and may, for example, be a positioning accuracy of 1 mm. The scanner 20 comprises a magnet 24, which produces a magnetic field $B_0$ for the imaging procedure. The scanner 20 furthermore comprises a gradient coil 25 and a RF coil 26. The RF coil 26 produces a magnetic field necessary to rotate the spins by 90° or 180°. The RF coil 26 also detects the signal from the spins within the body.

The magnet 24, gradient coil 25 and RF coil 26 are located in a scan room of the MRI scanner, which is surrounded by a shield 27 for preventing the high power RF pulses from radiating out through the room where the scanner 20 is positioned. It furthermore prevents irradiation coming from e.g. television or radio stations from being detected by the scanner 20.

The key component of the scanner 20 is the controller 23 as it controls all components of the scanner 20. A first component that is controlled by the controller 23 is a RF pulse generating means 28. The RF pulse generating means 28 may comprise a RF source for producing a sine wave or any other desired shape, such as a triangular waver or a square wave, of a desired frequency and a pulse programmer for shaping the RF pulses. The RF pulse generating means 28 may furthermore comprise a RF amplifier (not represented in FIG. 6) which increases the pulses' power from milli Watts to kilo Watts. The controller 23 furthermore controls a gradient pulse generating means 29 for setting the shape and amplitude of the gradient field. The gradient pulse generating means 29 may comprise a gradient amplifier for increasing the power of the gradient pulses to a level sufficient to drive the gradient coils 25. As already described above, the controller 23 may also control the position of the table 21.

The controller 23 may include a computing device, e.g. microprocessor, for instance it may be a micro-controller. In particular, it may include a programmable scanner controller, for instance a programmable digital logic device such as a Programmable Array Logic (PAL), a Programmable Logic Array, a Programmable Gate Array, especially a Field Programmable Gate Array (FPGA). The use of an FPGA allows subsequent programming of the scanner device 20, e.g. by downloading the required settings of the FPGA.

In accordance with the present invention, the controller 23 furthermore controls a means 30 for applying a time-varying external stimulus to the contrast agent having at least one exchangeable entity and being inside the patient 22, in order to saturate the at least one exchangeable entity. The external stimulus may generally be applied by using the same antenna as is used for the actual MRI image. Although, in other embodiments, the use of another antenna may also be applied for the application of an external stimulus.

According to the preferred embodiment of the first aspect of the invention, the means 30 for applying a time-varying external stimulus to the contrast agent may be a means for applying a time-varying RF saturation pulse in order to saturate the at least one proton of the CEST contrast agent.

The controller 23 itself may be controlled by an operator which gives input to the controller 23 through an input means 31, which may be a pointing device such as a keyboard or a mouse. An imaging sequence may be selected and customized from the input means 31. The operator can see the image on a display 32. In other embodiments, the operator can make hard copies of the images on a printing device such as a film printer or the like (not shown in the figure). Correlation between known parameter data used for generating the time-varying external stimulus, e.g. a known time course, and the time course resulting from the images may be implemented by using a suitable computer program.

Figure 7:
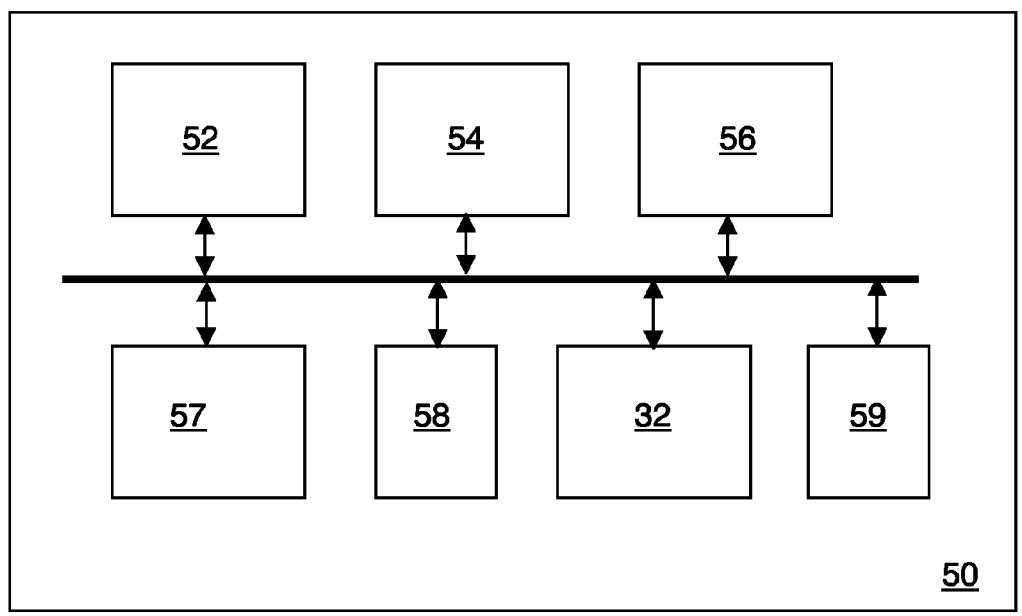
FIG. 7 illustrates a processing device for use with a device according to the present invention.

The controller 23 shown schematically in FIG. 6 is a processing system that typically has a configuration of one or more standard computer systems (in general "processing systems"). A typical processing system 50, as illustrated in FIG. 7, may include a bus 51, a processing unit (processor, CPU) 52, at least one memory device (e.g. random access memory, RAM, and/or read only memory, ROM) 54, a mass storage device 56, an internet interface 57, a network interface card (NIC) 58, a display 32, and various other input/output devices 59. The mass storage device 56 may include a magnetic, optical, or other equivalent storage medium. The internet connection device 57, if included, may be any device used to connect to the internet, and exemplary connection devices include, but are not limited to: a modem, a digital subscriber line (DSL) modem, a cable modem, an optical connection device, a T1 interface, a T3 interface, an E-1 interface and an E-3 interface. The input/output devices 59 may include a pointing device 31 such as a mouse and a keyboard.

A data processing system such as processing system 50 may also include application programs, operating systems, data, etc. which are not shown in FIG. 7 for the sake of clarity. It will be understood that such a data processing system may also include numerous elements not shown, such as disk drives, keyboards, display devices, network connections, additional memory, additional processing units, LANs, input/output lines, etc. For example, the processing system 50 may actually include multiple physical and logical devices connected in a distributed architecture.

Accordingly, the network interface card 58 is used to provide data communication with other devices that are part of processing system 50.

Furthermore, the present invention includes a computer program product which provides the functionality of a method according to the present invention. Further, the present invention includes a data carrier such as a CD-ROM or a diskette which stores the computer product in a machine-readable form and which executes at least one of the methods of the invention when executed on a computing device such as the controller 23. Nowadays, such software may be offered on the Internet or a company Intranet for download, hence the present invention includes transmitting the computer product according to the present invention over a local or wide area network. The computing device may include one of a microprocessor or an FPGA.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A method for MRI imaging, the method comprising:
after administering a contrast agent, repeatedly acquiring image data, including modulating contrast enhancement of the contrast agent in time by applying a time-varying radio frequency saturation pulse to said contrast agent, the time-varying radio frequency saturation pulse having a known pulse time course;
reconstructing the image data into image pixels or voxels of at least one of images and a part of the images with contrast enhancements;
determining an intensity time course of the at least one of the images and the part of the images with contrast enhancement;
correlating said intensity time course with the pulse time course of the applied time-varying radio frequency saturation pulse for each image pixel or of the reconstructed images or parts of the images with contrast enhancement to determine a presence of said contrast agent in each image pixel or voxel; and
displaying on a display device at least one of the reconstructed images, the part of the images with contrast enhancement, and a depiction of the presence of contrast agent for a selected image pixel or voxel.

2. The method according to claim 1, wherein said contrast agent comprises at least one exchangeable entity having a nuclear spin and a nuclear spin resonance frequency and having a first and a second exchangeable position, wherein, as a result of the time-varying radio frequency saturation pulse, the exchangeable entity changes between the first and the second exchangeable position, thereby inducing a change in its nuclear spin resonance frequency.

3. The method according to claim 1, further including:
repeating acquisition of parts of the image until all parts of the image have been repeatedly acquired; and
reconstructing the image.

4. The method according to claim 2, wherein the contrast agent is a CEST contrast agent.

5. The method according to claim 1, wherein applying a time-varying radio frequency saturation pulse is performed by varying at least one of power, offset frequency, shape, multiplicity, duration or intervals between said radio frequency saturation pulses for modulating the contrast enhancement.

6. The method according to claim 1, wherein modulating the contrast enhancement comprises switching the contrast enhancement on and off.

7. A device for performing MRI imaging, the device comprising:
an input device which inputs parameter data for a time-varying radio frequency saturation pulse and a contrast agent to generate image data; and
a processor programmed to:
reconstruct the image data into image pixels or voxels of at least a part of images,
calculate an intensity time course of each reconstructed at least part of the images, and
correlate said calculated intensity time course with the input parameter data of the time-varying radio frequency saturation pulse, image pixel by image pixel or image voxel by image voxel, for determining a presence of said contrast agent in a selected one of the image pixels or voxels.

8. The device according to claim 7, wherein the input parameter data includes a time-varying radio frequency pulse time course.

9. A non-transitory machine readable data storage device storing the computer program which controls one or more processors to:

after administration of a contrast agent, repeatedly acquire an image data for at least part of an image, the acquiring of the image data including modulating contrast enhancement of the contrast agent in time by applying a time-varying radio frequency saturation pulse to said contrast agent, the time-varying radio frequency saturation pulse having a known pulse time course;

reconstruct at least a part of an image, with the intensity time course of the part of the image, the image including an array of image pixels or voxels;

correlate said intensity time course with the pulse time course of the applied time-varying radio frequency saturation pulse for at least one selected pixel or voxel of the at least part of the image to determine a presence of said contrast agent in the selected image pixel or voxel; and display on a display device at least one of the reconstructed image part and an indication of the presence of the contrast agent in the selected at least one image pixel or voxel.

10. A controller for an MRI imaging device, the controller comprising:

an input device which obtains data relating to formation of a time-varying radio frequency saturation pulse, a control device which controls the MRI imaging device to apply the time-varying radio frequency saturation pulse based on the obtained data to a subject to which a contrast agent has been administered to generate contrast enhanced image data; and a computer programmed to correlate an intensity time course determined from the image data with a time course of the applied time-varying radio frequency saturation pulse to determine contrast agent influenced tissue parameters in image pixels or voxels of at least part of an image reconstructed from the contrast enhanced image data.

* * * * *